(12) United States Patent
White (10) Patent No.: US 7,407,440 B2
(45) Date of Patent: Aug. 5, 2008

(54) DRIVE SHAFT COUPLING

(75) Inventor: Patrick M. White, Downingtown, PA (US)

(73) Assignee: Precimed S.A., Orvin (CH)

( * ) Notice: Subject to any disclaimer, the term of this patent is extended or adjusted under 35 U.S.C. 154(b) by 0 days.

(21) Appl. No.: 11/457,471

(22) Filed: Jul. 14, 2006

(65) Prior Publication Data

US 2006/0287116 A1    Dec. 21, 2006

Related U.S. Application Data (60) Division of application No. 10/043,423, filed on Jan. 10, 2002, now Pat. No. 7,150,680, which is a continuation-in-part of application No. 09/860,918, filed on May 18, 2001, now Pat. No. 6,513,814, which is a continuation-in-part of application No. 09/523,719, filed on Mar. 11, 2000, now Pat. No. 6,257,593, which is a continuation-in-part of application No. 09/311,938, filed on May 14, 1999, now abandoned.

(60) Provisional application No. 60/262,362, filed on Jan. 19, 2001.

(51) Int. Cl.
  *F16D 7/02*    (2006.01)

(52) U.S. Cl. .................................... 464/30; 464/902
(58) Field of Classification Search ............... 464/30, 464/51, 89, 182, 183, 902; 403/278, 281, 403/282; 285/255, 307, 345
See application file for complete search history.

(56) References Cited

U.S. PATENT DOCUMENTS

| | | | | |
|---|---|---|---|---|
| 2,868,001 A | * | 1/1959 | Russell | 464/30 |
| 3,140,107 A | * | 7/1964 | Hynes | 403/281 X |
| 5,273,519 A | * | 12/1993 | Koros et al. | |
| 5,816,923 A | * | 10/1998 | Milo et al. | 464/902 |
| 6,078,831 A | * | 6/2000 | Belef et al. | |
| 6,361,442 B1 | * | 3/2002 | Dillenberger et al. | 464/30 |

* cited by examiner

*Primary Examiner*—Greg Binda
(74) *Attorney, Agent, or Firm*—Moetteli & Associés SàRL (57) ABSTRACT

A flexible torque-transmitting coupling assembly and method is disclosed, as well as flexible surgical reamers having such assemblies. The reamers employ a fitting with radially flexible member, e.g., a split collet or a super-elastic collar that receives an elongated tubular shaft of super-elastic alloy. A compression sleeve is applied to the collet, in one embodiment, while the collar is located within a counter-bore of the fitting in another embodiment. Relative motion between the shaft, fitting and collet (or collar) induces a super-elastic activation in the shaft to form the desired coupling.

21 Claims, 4 Drawing Sheets

DRIVE SHAFT COUPLING

RELATED APPLICATIONS

This application is a divisional application of U.S. application Ser. No. 10/043,423 filed Jan. 10, 2002 of the same title (now U.S. Pat. No. 7,150,680) which is a continuation-in-part application of U.S. application Ser. No. 09/860,918, filed May 18, 2001 and entitled, "Stress-Induced Connecting Assembly", (now U.S. Pat. No. 6,513,814), which is a continuation-in-part of Ser. No. 09/523,719, filed Mar. 11, 2000 and entitled, "Stress-Induced Interposed Connector" (U.S. Pat. No. 6,257,953), which is a continuation-in-part of Ser. No. 09/311,938, filed May 14, 1999 and entitled "Stress-Induced Seal", now abandoned. This application is further based on prior Provisional Application Ser. No. 60/262,362, filed Jan. 19, 2001 and entitled Drive Shaft Coupling. The entire disclosures of these afore-mentioned applications are expressly incorporated by reference herein and relied-upon.

TECHNICAL FIELD

This invention relates generally to torque-transmitting assemblies that have fittings coupled to a flexible drive shaft made of a super-elastic alloy, useful in devices for medical and industrial applications where a flexible shaft is necessary; and in particular to powered surgical instruments for transmitting torque to "flexible reamers" or "flexible drills" to remove material from the center of curved bones during orthopedic surgery.

BACKGROUND OF THE INVENTION

The use of metallic super-elastic alloys, such as Ni—Ti (nitinol) and other bi- or tri-metal alloys, has been documented in a variety of technical applications, including fasteners, connectors, gaskets, clamps and seals. Many such uses have required temperature in order to activate the material and change its physical state, while others have used mechanical forces that impart stress to cause a super-elastic physical deformation in the material. Of particular concern to the instant inventor is the application of the super-elastic material to connectors. The use of non-corrosive, metallic super-elastic material offers a decided advantage in high performance connecting assemblies, versus more conventional connectors requiring threaded fasteners, springs, clamps or other holding or securing mechanisms. Particularly it can withstand more wear than alloys used in conventional connectors due to its harder surface characteristics. It can also withstand extreme vibrations and not loosen due its elastic preloaded condition without using conventional adhesives to hold the assembled components and/or the connector itself together. Adhesives used with conventional connectors make them very difficult to disassemble, whereas it is generally possible to make a super-elastic connector completely reversible.

U.S. Pat. Nos. 5,395,193 and 5,584,631 to Krumme et al., discuss the use of nickel-titanium shape memory retainers in an optimized elastic condition that have super-elastic or pseudo-elastic properties. These fasteners are said to be useful for eyeglass assembly; they are placed onto a pin to retain components together.

It is commonly known that nitinol (formally known as Nickel Titanium Naval Ordinance Laboratory, but other super-elastic nickel-titanium alloys being included in this definition) tubing, wire or rod can be used as a mechanical drive shaft. The use of metallic super-elastic alloys, such as Ni—Ti (nitinol) and other bi- or tri-metal alloys, has been documented in a variety of technical applications, including fasteners, connectors, gaskets, clamps and seals. Many such uses have required temperature in order to activate the material and change its physical state, while others have used mechanical forces that impart stress to cause a super-elastic physical deformation in the material. Of particular concern to the instant inventor is the application of the super-elastic material to connectors. The use of non-corrosive, metallic super-elastic material offers a decided advantage in high performance connecting assemblies, versus more conventional connectors requiring threaded fasteners, springs, clamps or other holding or securing mechanisms. Particularly it can withstand more wear than alloys used in conventional connectors due to its harder surface characteristics. It can also withstand extreme vibrations and not loosen due its elastic pre-loaded condition without using conventional adhesives to hold the assembled components and/or the connector itself together. Adhesives used with conventional connectors make them very difficult to disassemble, whereas it is generally possible to make a super-elastic connector completely reversible.

U.S. Pat. No. 5,683,404 to Johnson, entitled "Clamp and Method for its Use", further discusses shape memory materials that are "pseudo-elastic", defining these materials to be super-elastic, because of their ability to exhibit super-elastic/pseudo-elastic recovery characteristics at room temperature. In other words, a material is super-elastic when, if sufficient stresses are applied, such materials exhibit martensitic activation (i.e., deform from an austenitic crystal structure to a stress-induced structure postulated to be martensitic in nature), returning thence to the austenitic state when the stress is removed. The alternate crystal structures described give the alloy super-elastic or pseudo-elastic properties. Poisson's Ratio for nitinol is about 0.3, but this ratio significantly increases up to approximately 0.5 or more when the shape memory alloy is stretched beyond its initial elastic limit. It is at this point that stress-induced martensite is said to occur, i.e., the point beyond which the material is permanently deformed and thus incapable of returning to its initial austenitic shape. A special tool is employed by Johnson to impart an external stretching force that deforms the material which force is then released to cause the material to return to its original condition. While the device is stretched, a member is captured by it and securely clamped when the stretching force is released. This device is intended for use in clamping and does not contemplate traditional connecting operations of the kind addressed by the present invention. Another use envisioned by Johnson is in connecting the modular components of a medical device, as described in his U.S. Pat. No. 5,858,020, by subjecting a thimble component made of shape memory material to an external stretching stimulus to elongate and thereby reduce its transverse dimension. Upon release of the stretching force, this component returns towards its original rest dimension, contacting and imparting a force on another component. This is a sequential stretching and relaxation of the super-elastic material rather than a simultaneous activation and retention operation. Also, special structures are necessary on the thimble to allow the stretching force to be imparted.

In U.S. Pat. No. 5,197,720 to Renz, et al., a work piece is held within a clamping tool by an expansion element made of shape memory material that is activated by mechanical force. In this way, torque is transmitted through the shape memory member. This device is useful for bringing parts together for holding the work piece in order to perform an operation. It does not, however contemplate a use as a connector. U.S. Pat. No. 5,190,546 to Jervis discloses insertion into a broken bone cavity of a split member made of shape memory material using a super-elastic alloy. The split member holds the walls of the bone cavity when radial compressive forces acting on it are released. In order for the radial compressive force to reduce the diameter, the component must be split, allowing the reduction in dimension for insertion. It does not act as an interposed member in a connecting assembly.

Others have sought to utilize the properties of shape memory materials as locking, connector and bearing elements, e. g., U.S. Pat. No. 5,507,826 to Besselink., et al, U.S. Pat. No. 5,779,281 to Kapgan, et al., and U.S. Pat. No. 5,067,827 to Arnold, respectively; however, such approaches have required temperature to be applied during use. U.S. Pat. No. 5,277,435 to Kramer, et al. and U.S. Pat. No. 5,876,434 to Flomenblit et, al. similarly has relied upon temperature to activate the shape memory effect. Such dependence on extrinsic activation by temperature introduces an added process step and may further be disadvantageous in certain other applications.

U.S. Pat. No. 5,842,312 to Krumme, et al., entitled, "Hysteretic Damping Apparati and Methods", employs shape memory tension elements to provide energy dissipation. Such elements can be placed between building structures, etc., which are subject to vibration, serving to absorb the energy created by their relative movement. However, this patent does not contemplate the vibration dampening effect of a super-elastic material in the formation of a connector.

Nitinol is especially useful for transmitting torque while in a bowed or bent shape. These types of drive shafts have proven useful in orthopedic surgical applications where drilling or reaming of curved bones is necessary. One application is to use a drill or reamer with a nitinol drive shaft to clean out the center of a femoral bone before implanting a prosthesis or femoral nail. These bones typically have a bow with a 90-inch radius and require a flexible reamer for the procedure. Nitinol tubing can be used for this application since it is cannulated and can be passed over a guide wire that is placed down the femur before the reaming process begins. Since the tubing is solid it is very easy to clean after the surgical operation since there are no crevices for blood to get trapped in. Earlier designs utilized spring drive shafts and cleaning was extremely difficult since blood could get trapped between the windings of the spring. The earlier spring designs also had difficulties when run in the reverse direction since springs tend to be strong while being used in one direction, however when run in the opposite direction they tend to unwind. To prevent this unwinding problem several manufacturers have added an additional spring inside of the primary spring, which is wound in the opposite direction. Since one spring is inside of the other this contributes to the difficulties with cleaning and further obviates the need for an alternative shaft design.

With the market demand increasing for these novel nitinol drive shafts there have been many attempts to develop safe coupling methods for attachment to the shaft. One difficulty that engineers have been faced with is presented when nitinol tubing exceeds its torsional or fatigue stress limits; it has been known to fail catastrophically and fragment into several sharp pieces. This is dangerous when inside of a patient and poses severe concerns if these types of products are to be used reliably. Historically there have been no solutions offered to limit the stress in the drive shaft, which would eliminate the presently lingering concerns over breakage during use.

Another difficulty is presented with the attachment of the fittings to the nitinol drive shaft. The connection must be reliable and not create any unnecessary stress on the tubing. This will lead to early failure of the shaft. Typically in the orthopedic reamer example mentioned above one end of the nitinol tube has a stainless steel fitting which attaches to a power instrument and on the opposite end either a stainless steel reamer head or an intermediate modular fitting that connects to a reamer head. Several attempts to create reliable attachments have been made.

One approach to the above-mentioned attachment problem has been to use an epoxy to "glue" the fittings onto the nitinol shaft. However, temperatures in the sterilization process and the criticality of surface preparation have rendered this approach unreliable.

Another approach has been to attach the fitting to the shaft with a laser weld; however, the welding process embrittled the tubing and it was known to fail torsional demands in testing. A cross hole and pin were placed through the fittings, however this added approach further proved useless since the matching hole in the tubing created a tremendous stress riser in the tubing causing failure at very low torsional values. In the example mentioned it was known to fail anywhere between 2 to 4 N-M.

Yet another approach has been to press fit the nitinol shaft into a fitting with approximately 0.002-inch interference. Initial trials worked, however when put through rigorous fatigue tests the tubing placed too much hoop stress on the fittings causing them to fail rather than the shaft. The solution proposed to fix that problem was to add a long section on the fitting that was loosely fit around the tube. This would allow the stress to transition slowly into the area where the press fit was done. This worked successfully, however the solution created a need for the fitting to be extremely long in comparison to the reamer heads being used. This is undesirable since the reamer must follow the curvature of the bone and it did not solve the issue of limiting the torque in the shaft to ensure the safety of the drive shaft during use.

Thus, there remains a primary need to provide a coupling system that is safe and effective for use in surgical and industrial applications where flexible drive shafts are necessary.

Accordingly, there is a need to form a connecting assembly using a durable metallic, non-corrosive connector assembly, which are simple to install using relative motion to activate the assembly.

There is a further need to form a secure connection between components that minimizes the micro-motional wear characteristics of the assembly, enhancing its useful life.

There is another need to form a fastened assembly that does not require temperature for its activation.

There is still a need to form an assembly using a fastener that adjusts for differences in thermal coefficients of expansion or contraction of dissimilar materials comprising those components being fastened.

There is still a further need for a connector with elastic properties that allow more forgiving tolerances during manufacturing of the assembly components.

There is another need to use a nitinol drive shaft to replace the spring drive shafts in orthopedic instruments and many industrial tools to simplify the cleaning process and ensure consistent torque resistance in the forward and reverse directions.

There is a further need to provide a coupling system which will limit the torque in the nitinol drive shaft fitting to ensure that the coupling limits the torque before the tubing breaks.

There is yet a need for a coupling that will not place any unnecessary stress on the nitinol tubing causing it to prematurely break.

There is also a need to shorten the length of the fitting so that the reamer can follow the natural contour of the inside of the bone while transferring the stress smoothly so as to ensure the strength of the fitting.

SUMMARY OF THE INVENTION

According to the invention, a torque-transmitting assembly is described, as well as a method of forming the assembly and a surgical reamer that includes the assembly. The assembly has a female coupling member with a bore. The female coupling member may be a fitting that connects to a power instrument or it may present a cutting head, or both. A radially flexible member is received within the bore, defining a hollow shape with an opening. The assembly also has an elongated shaft member made of a super-elastic alloy, received within the opening. Relative motion among the members causes the radially flexible member to contact the shaft, inducing a super-elastic activation in the shaft that urges the shaft and radially flexible member into surface-to-surface contact, securing the members together in a fixed relative position. In a preferred embodiment, the radially flexible member has an external surface that frictionally engages the bore upon relative motion. The contact still preferably occurs along one or more areas that frictionally carry the applied torque, which contact area may be calibrated so that the contact slips at a preset torque before the failure strength of the shaft is reached. In another preferred embodiment, the shaft is tubular with a cannulation, which may further be aligned with another cannulation in the female coupling member for common passage of a guide wire. In yet another preferred embodiment, an inter-positional polymer sleeve is provided in the assembly for transmitting bending stress. In a still another preferred embodiment, the female coupling member has a counter-bore, while the radially flexible member has an exterior surface adapted for engagement within the counter-bore and may be compressed within the counter-bore or be in a pre-assembled state therein. In one alternative, preferred embodiment, the radially flexible member has a split collet, whereupon relative motion among at least two of the members causes the opening to contact the shaft, inducing a super-elastic activation in the shaft that urges the shaft and the collet into surface-to-surface contact, securing the members together in a fixed relative position. In another alternative, preferred embodiment, the radially flexible member is a collar and made of super-elastic alloy, whereupon relative motion between the fitting and the collar causes the collar to contact the shaft, inducing a super-elastic activation in the shaft that engages the shaft and collar into surface-to-surface contact, securing the members together in a fixed relative position. The collar may further be a washer or a series of washers.

A method of forming a torque-transmitting assembly is also disclosed, having the following steps. A female coupling member is provided, with a bore, as is a radially flexible member with an external surface and an opening, the radially flexible member being situated within the bore. An elongated shaft member is provided, made of a super-elastic alloy, and is received within the opening. Relatively moving at least two of the members, causes the radially flexible member to contact the shaft, inducing, a super-elastic activation in the shaft that urges the shaft and radially flexible member into surface-to-surface contact, securing the members together in a fixed relative position. The radially flexible member may alternatively consist of either a split collet operable with an outer compression sleeve, or a super-elastic collar operable within a counter-bore of the female coupling.

A flexible surgical reamer having a torque-transmitting assembly is also disclosed. The assembly includes a female coupling member, which may be a fitting with a counter-bore that is further provided with a head presenting a cutting tool-bit, or may be an outer compression sleeve. A radially flexible member is provided, which may be a collar member made of super-elastic alloy with an opening, preferably a washer or series of washers, located in the counter-bore. Relative motion among the members causes the opening to contact the shaft, inducing a super-elastic activation in the shaft that urges the shaft and the collar into surface-to-surface contact, securing the members together in a fixed relative position. Alternatively, the radially flexible member may have a split collet with an exterior surface received in the sleeve, and an opening. The assembly has an elongated shaft member made of a super-elastic alloy, received within the opening. Relative motion among the members causes the opening to contact the shaft, inducing a super-elastic activation in the shaft that urges the shaft and the collet into surface-to-surface contact, securing the members together in a fixed relative position. It is desirable that the contact occurs along an area that frictionally carries the applied torque and is calibrated to slip at a preset torque before the failure strength of the shaft is reached. An inter-positional polymer sleeve may be additionally provided for transmitting bending stress in the assembly. The shaft may be tubular, with a cannulation, likewise the female coupling member may have a cannulation that aligns with the shaft cannulation for passage of a guide wire through the reamer.

An advantage of the present invention is a torque-transmitting coupling assembly that is also torque-limiting, relying upon a surface-to-surface frictional contact, thus slippage of the coupling occurs at torque less than the maximum failure strength of the shaft.

Another advantage of the present invention is that the torque clan be adjusted, by increasing or decreasing the area of contact in interference and adjusting the surface finishes on the assembly components.

A further advantage is the amelioration of fatigue due to hoop stress by use of a preferred softer material, such a polymer sleeve interposed between the coupling member and the shaft—this acts as a dampener to spread out the forces smoothly ensuring the proper stress transfer.

Other objects and advantages of the invention will become apparent upon reading the following Detailed Description and upon reference to the appended Drawings.

DETAILED DESCRIPTION

Figure 1:
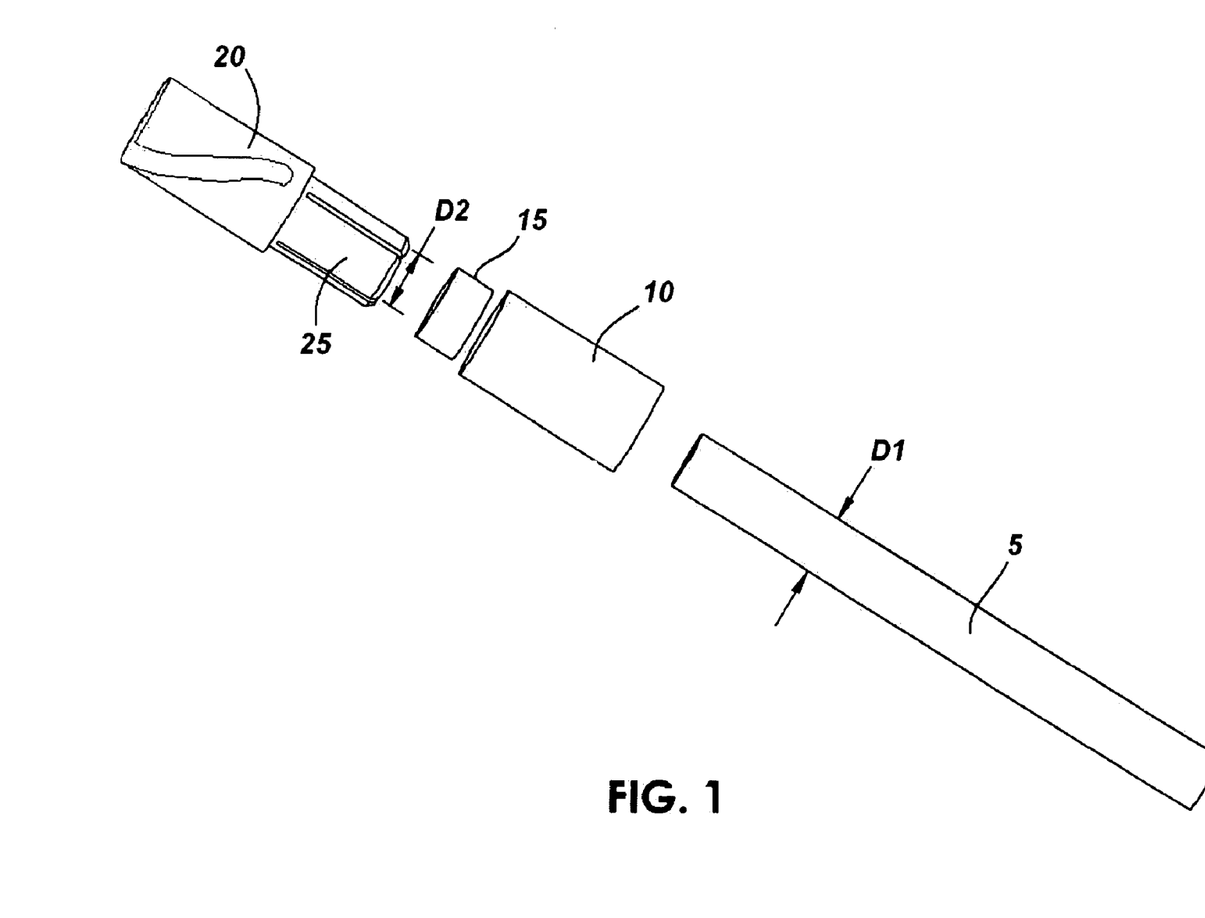
FIG. 1 is an exploded view of a torque-transmitting assembly of the present invention, showing a preferred fitting formed with a split collet, a compression sleeve and an optional polymer sleeve interposed therebetween.
Figure 2:
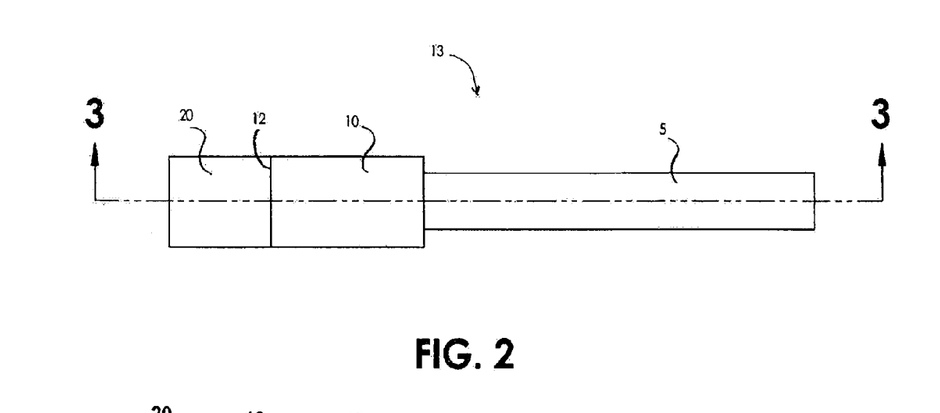
FIG. 2 is an elevational view of FIG. 1, showing the collet compressed by the sleeve to couple the assembly.
Figure 3:
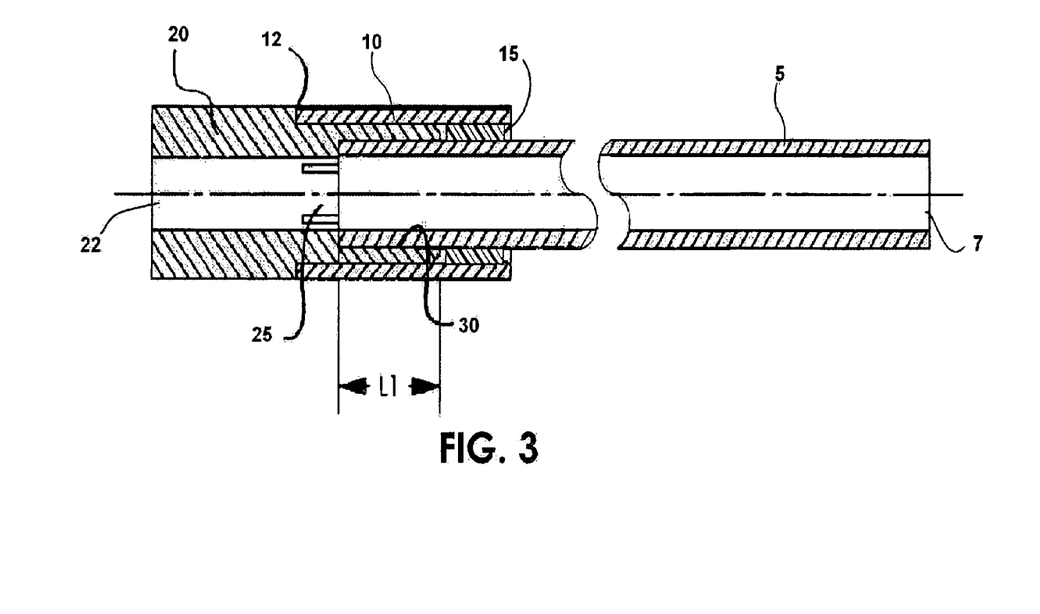
FIG. 3 is a sectional view taken substantially along the Lines 3-3 of FIG. 2.
Figure 4:
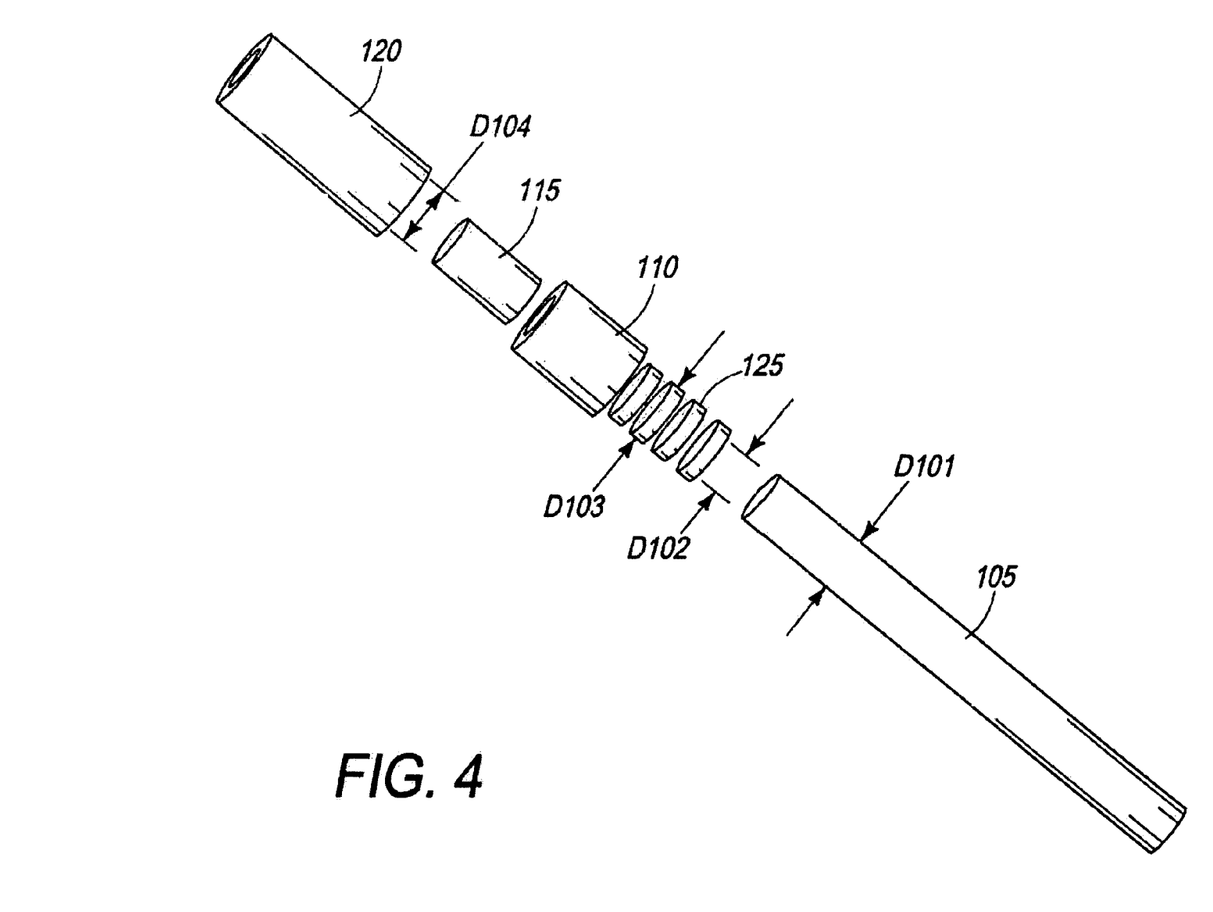
FIG. 4 is an exploded view of another embodiment of a torque-transmitting assembly of the present invention, showing a fitting with a collar preferably having a series of washers each made of super-elastic alloy, a compression sleeve and an optional polymer sleeve.
Figure 5:
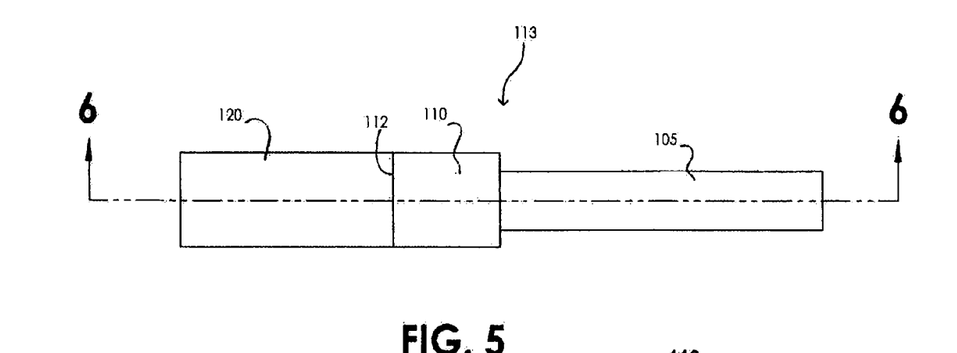
FIG. 5 is an elevational view of FIG. 4, showing the collar compressed by the sleeve to couple the assembly.
Figure 6:
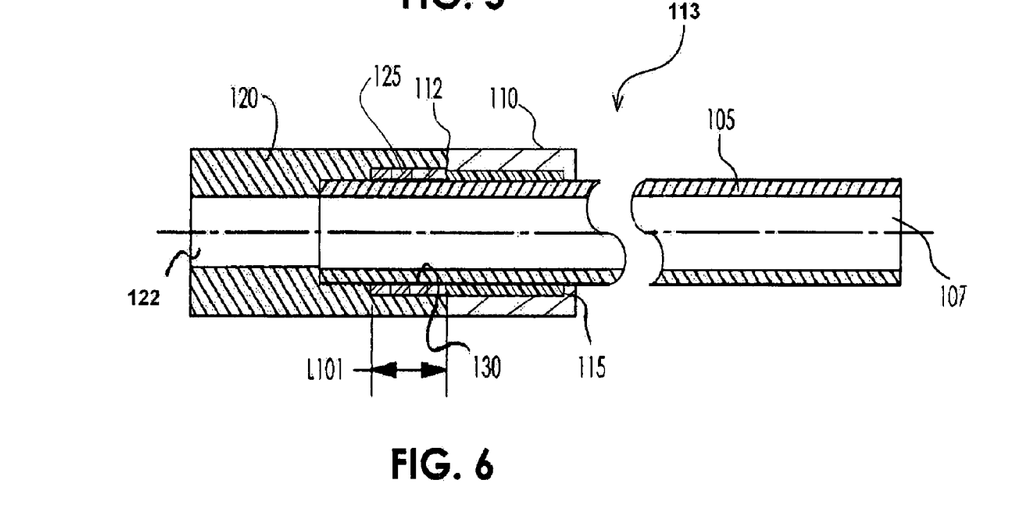
FIG. 6 is sectional view taken substantially along the Lines 6-6 of FIG. 5.

Referring to FIGS. 1-3 and particularly FIG. 1, the present invention includes a drive shaft 5 made of a super-elastic alloy, preferably a nickel-titanium commonly known as nitinol. Shafts made from this type of alloy can be formed with a cannulation 7 as shown in FIG. 3 and exhibit the distinctive characteristic of transferring torque while subjected to high bending forces during use. The exemplary use of the present invention is in orthopedic drilling and reaming devices; however, the usage of super-elastic alloys according to the invention has much broader applications encompassing both medical as well as other industrial applications. A device of the present invention is generally shown at 13 in FIGS. 2-3. Tool fitting 20 may be a cutting tool fitting (as shown in FIG. 1) and preferably has a cannulation 22 that is aligned with another cannulation 7 formed in shaft 5 when device 13 is assembled according to the present method. The aligned cannulations 7, 20 allow device 13 to be placed over the top of a guide wire (not shown). Tool fitting 20 also has a radially moveable, i.e., flexible collet portion 25, which is preferably an integral structure although the fitting may be separate from the radially flexible, split portion as discussed below in conjunction with another embodiment (FIGS. 4-6). According to the present method, shaft 5 is slid into collet 25. Preferably there is an interference fit between the outer diameter D1 of shaft 5 and the inner diameter D2 of collet 25. This interference causes collet 25 to bend out in a flower configuration as shaft 5 and fitting 20, are slid together.

Once tubular shaft 5 has been slid into collet 25, a compression sleeve 10 (FIGS. 1-3) is slid over the flower shaped collet 25 and welded at junction 12. As these components 5, 10, 25 are assembled, the collet 25 is forced radially onto the shaft causing a super-elastic activation of the alloy forming the shaft to thereby effect a secure coupling. This super-elastic reaction allows the fingers of collet 25 to contact the tube along the length L1 as shown in FIG. 3. This surface-to-surface contact (shown at 30 in FIG. 3) allows the device 13 to transmit torque. In essence the components are transmitting torque via friction. Thus, whenever the frictional forces are overcome by application of too much torque to the tool fitting 20, the fitting and shaft 5 break free of one another to slip rotationally. This slippage limits the amount of torque that can be applied to the shaft. The contact surface 30 can be adjusted by design to change the length L1, in turn, adjusting the maximum applicable torque limit to ensure that the slippage occurs before the maximum yield strength is reached in shaft 5.

Compression sleeve 10 may have an optional polymer sleeve 15 pre-assembled inside. The purpose of polymer sleeve 15 is to transfer stress through tool fitting 20 in a uniform manner to shaft 5 during its use in a bent configuration. This smoother transition ensures against premature failure of fitting 20. Use of polymer sleeve 15 may be found necessary when the design of the wall thickness of tool fitting 20 becomes thin, e.g., between about 0.25 mm to 1.00 mm. Otherwise, tool fitting 20 will be able to handle the stress eliminating the necessity for polymer sleeve 15.

Another preferred embodiment of the present invention is depicted in FIGS. 4-6, particularly FIG. 4, which shows a shaft 105 made of super-elastic alloy such as nitinol. As discussed relative to FIGS. 1-3, shaft 105 is similar, preferably having a cannulation 107 as shown in FIG. 6. Shaft 105 thus can exhibit the distinctive characteristic of transferring torque while exposed to high bending forces during use. Although the exemplary uses of super-elastic alloy herein are orthopedic drilling and reaming devices, use of this alloy in the present invention has much broader applications encompassing both medical as well as other industrial applications. The assembled device is generally shown at 113 in FIGS. 5-6 and utilizes a tool fitting 120 that is modular rather than a unitary component (see collet 25 in FIGS. 1-3). Tool fitting 120 may have a cannulation 122, which is useful while aligned with the shaft cannulation 107 to allow it to be placed over the top of a guide wire (not shown). Tool fitting 120 is sized with inner diameter counter-bore D104 and has a modular radially flexible portion comprising a series of nitinol washers 125 that together are collar-shaped. Washers 125 each have an outer diameter D103 and an inner diameter D102. During assembly according to another preferred method of the present invention, shaft 105 having diameter D101 is slid into the tool fitting 120. Preferably upon assembly there is an interference fit between the outer diameter D101 and the inner diameter D102 and an interference fit between the outer diameter D103 of the washer collar 125 and the inner diameter of the counter bore D104. This interference causes a radial compression in the flexible collar washers 125 causing surface-to-surface contact as shown at 130 along length L101. The radially, flexible washers 125 end up interposed between the shaft 105 and the tool fitting 120. This can be accomplished through various assembly methods. In one instance the flexible washers 125 can be pre-assembled with the tool fitting 120 and then the shaft 105 can subsequently be introduced to the assembly. Preferably though, the shaft 105 can be loosely placed in the tool fitting 120 and then the washers can be advanced into the tool fitting 120. As they are slid into place they compress via interference between the outer dimension D103 of the washers 125 and the inner dimension D104 of the tool fitting. This interference causes a super-elastic reaction in the washers 125 causing their inner dimension D102 to compress against the shaft's 105 outer dimension D101 causing the surface-to-surface contact as shown at 130 along length L101. It is this surface to surface contact shown at 130 in FIG. 6 that allows the assembly to transmit torque. In essence the components are transmitting torque-using friction. If the frictional forces are overcome by applying too much torque to the tool fitting 120 the components 120,105 break free and slip rotationally. This rotational slip limits the amount of torque that can be applied to the shaft. If the contact surface 130 is adjusted during design by changing the length L101 the maximum applicable torque limit can be adjusted to ensure that the slippage occurs before the maximum yield strength is reached in the shaft 105.

An additional sleeve 110 can be added and welded at junction 112 with an optional polymer sleeve 115 pre-assembled inside. The purpose of the polymer sleeve is to transfer bending stress through the tool fitting 120 in a uniform manner to the shaft 105 during use in a bent configuration. This smoother transition ensures against premature failure of the fitting. The use of this polymer sleeve 115 may only be necessary when the design of the wall thickness of the tool fitting 120 becomes thin, somewhere on the order of 0.25 mm to 1 mm. Otherwise the tool fitting 120 will be able to handle the stress eliminating the necessity for the additional polymer sleeve 115 and sleeve 110.

Although the invention his been described with reference to preferred embodiments thereof, it is evident to those of skill in the art that various modifications and improvements may be made without departing from the spirit and scope of the invention as defined by the appended claims.

What is claimed is:

1. A torque-transmitting assembly comprising:
   a) a female coupling member with a bore;
   b) a radially flexible member, received within the bore, defining a hollow shape with an opening, the radially flexible member being made of super-elastic alloy; and
   c) an elongated shaft member made of a super-elastic alloy, received within the opening, wherein forcing the radially flexible member onto the shaft causes the radially flexible member to contact the shaft, inducing a super-elastic activation in the shaft and further induces a super-elastic activation of the radially flexible member that urges the shaft and radially flexible member into surface-to-surface contact, securing the members together in a fixed relative position.

2. The assembly of claim 1, wherein the super-elastic alloy is a nickel-titanium alloy.

3. A torque-transmitting coupling assembly comprising:
a) a tool fitting member formed with a counter-bore;
b) a collar member being a series of washers made of super-elastic alloy, having an exterior surface and an opening, the collar being located in the counter-bore; and
c) an elongated shaft member made of a super-elastic alloy, received within the opening,
whereupon relative motion between the fitting (120) and the collar (125) causes the collar (125) to contact the shaft (105), inducing a super-elastic activation in the shaft (105) that engages the shaft (105) and collar into surface-to-surface contact, securing the members (105, 120, 125) together in a fixed relative position.

4. The assembly of claim 3, wherein engagement of the exterior surface with the counter-bore compresses the opening against the shaft.

5. The assembly of claim 4, wherein the engagement occurs along one or more contact areas that frictionally carries the applied torque.

6. The assembly of claim 5, wherein the contact area is calibrated so that the coupling slips at a preset torque before the fatigue strength of the shaft is reached.

7. The assembly of claim 3, wherein the super-elastic alloy is a nickel-titanium alloy.

8. The assembly of claim 3, wherein the shaft is tubular with a cannulation.

9. The assembly of claim 8, wherein the fitting has a cannulation aligned with the shaft cannulation, for common passage of a guide wire there through.

10. The assembly of claim 3 further comprising an interpositional polymer sleeve for transmitting bending stress in the assembly.

11. The assembly of claim 3, wherein the fitting further comprises a cutting tool-bit.

12. An interference fit drive shaft coupling for a rotary surgical tool comprising:
a tool fitting (20) adapted to receive a rotary surgical cutting tool, the fitting (20) having a fitting cannulation (22);
a collet (25) in line and integral with the tool fitting (20), the collet having a compression sleeve (10) slid over it, and having a collet cannulation (22) concentric with the fitting cannulation (22) of the tool fitting (20), the collet cannulation (22) having a contact surface (30) with an inner diameter (D2); and
a flexible drive shaft (5) made of a nickel-titanium alloy and having a shaft cannulation (7), the nickel-titanium alloy having metal alloy properties selected from the group consisting of: martensitic properties and super-elastic properties and adapted to transfer torque while subjected to bending forces during use, the drive shaft (5) securely receivable in the collet (25) by an interference fit between an outer diameter (D1) of shaft (5) and the inner diameter (D2) of the contact surface (30) of the collet (25), the interference fit induced by a super-elastic activation in the shaft (5) that engages the shaft (5) and collet into surface-to-surface contact, and disposing the shaft (7) cannulation to be substantially concentric with the fitting cannulation (22) to provide said interference fit drive shaft coupling.

13. A torque-transmitting coupling assembly comprising:
a) a tool fitting member formed with a counter-bore;
b) a collar member being a washer made of super-elastic alloy, having an exterior surface and an opening, the collar being located in the counter-bore; and
c) an elongated shaft member made of a super-elastic alloy, received within the opening,
whereupon relative motion between the fitting (120) and the collar (125) causes the collar (125) to contact the shaft (105), inducing a super-elastic activation in the shaft (105) that engages the shaft (105) and collar into surface-to-surface contact, securing the members (105, 120, 125) together in a fixed relative position.

14. The assembly of claim 13, wherein engagement of the exterior surface with the counter-bore compresses the opening against the shaft.

15. The assembly of claim 14, wherein the engagement occurs along one or more contact areas that frictionally carries the applied torque.

16. The assembly of claim 15, wherein the contact area is calibrated so that the coupling slips at a preset torque before the fatigue strength of the shaft is reached.

17. The assembly of claim 13, wherein the super-elastic alloy is a nickel-titanium alloy.

18. The assembly of claim 13, wherein the shaft is tubular with a cannulation.

19. The assembly of claim 18, wherein the fitting has a cannulation aligned with the shaft cannulation, for common passage of a guide wire there through.

20. The assembly of claim 13, further comprising an interpositional polymer sleeve for transmitting bending stress in the assembly.

21. The assembly of claim 13, wherein the fitting further comprises a cutting tool-bit.

* * * * *

UNITED STATES PATENT AND TRADEMARK OFFICE
CERTIFICATE OF CORRECTION

| | | |
|---|---|---|
| PATENT NO. | : 7,407,440 B2 | Page 1 of 1 |
| APPLICATION NO. | : 11/457471 | |
| DATED | : August 5, 2008 | |
| INVENTOR(S) | : Patrick M. White | |

It is certified that error appears in the above-identified patent and that said Letters Patent is hereby corrected as shown below:

In Col. 8, line 53, replace the phrase "Although the invention his been described" with --Although the invention has been described--.

Signed and Sealed this

Twenty-eighth Day of October, 2008

JON W. DUDAS
*Director of the United States Patent and Trademark Office*